United States Patent [19]
Lambridis et al.

[11] Patent Number: 5,505,965
[45] Date of Patent: Apr. 9, 1996

[54] METHOD OF IMPROVING THE STABILITY OF COLORANT CONTAINING PARTICLES

[75] Inventors: George C. Lambridis, Wayne; Nathanial Goodwin, Newark, both of N.J.

[73] Assignee: Whittaker, Clark & Daniels, Inc., Plainfield, N.J.

[21] Appl. No.: 350,386

[22] Filed: Dec. 6, 1994

Related U.S. Application Data

[63] Continuation of Ser. No. 18,089, Feb. 16, 1993, abandoned.

[51] Int. Cl.⁶ ....................... A61K 9/14
[52] U.S. Cl. .............. 424/490; 424/59; 424/401; 106/437; 106/447; 106/448
[58] Field of Search .............. 424/490, 401, 424/59

[56] References Cited

U.S. PATENT DOCUMENTS

| | | | |
|---|---|---|---|
| 1,380,022 | 4/1974 | Twist et al. | 106/300 |
| 4,648,908 | 3/1987 | Taksuka et al. | 106/308 F |
| 5,143,722 | 9/1992 | Hollenberg et al. | 424/63 |

FOREIGN PATENT DOCUMENTS

| | | |
|---|---|---|
| 0220617 | 5/1987 | European Pat. Off. . |
| 0328906 | 8/1989 | European Pat. Off. . |
| 2134621 | 4/1972 | France . |
| 49-125539 | 12/1974 | Japan . |
| 52-32024 | 3/1977 | Japan . |
| 8604598 | 8/1986 | WIPO . |
| 9006103 | 6/1990 | WIPO . |

OTHER PUBLICATIONS

Patent Abstracts of Japan, vol. 13, No. 84, (C–572), Publication No. JP63270618, published Aug. 11, 1988, Patent Application No. JP870106078, (Kanebo Ltd.) by Mori Kenji.

Abstract, Japanese Patent Application, Publication No. JP52009442 B 770316 DW7715 (Derwent) by Shiseido KK.

*Primary Examiner*—Jyothsan Venkat
*Attorney, Agent, or Firm*—Brumbaugh, Graves, Donohue & Raymond

[57] ABSTRACT

A composition comprising colorant-containing particles having a coating comprising propylene glycol and a carrier component selected from the group consisting of carriers suitable for food, drug and cosmetic preparations and mixtures thereof.

5 Claims, 2 Drawing Sheets

METHOD OF IMPROVING THE STABILITY OF COLORANT CONTAINING PARTICLES

This application is a continuation of application Ser. No. 08/018,089, filed on Feb. 16, 1993, now abandoned.

The present invention relates to color compositions which have improved light stability and sun protection factor (SPF) properties. More specifically, the compositions of the present invention have an outer protective layer which absorbs ultraviolet light and thereby prevents the fading or discoloration of the colorant-containing particles. The outer layer further acts to impart an improved sunburn protection factor to the novel compositions of the invention.

BACKGROUND OF THE INVENTION

Color compositions are widely used in the cosmetic industry principally for aesthetic purposes. Accordingly, it is important that color compositions remain stable, i.e., not fade or discolor. One principal cause for discoloration of color compositions used in the cosmetic field is the tendency of colorants to absorb light, principally ultraviolet light, which results in the degradation of the colorant molecules.

In the past, efforts to improve the light stability of color compositions have involved generally the use of ultraviolet light absorbing compositions, such as benzophenones, and/or antioxidants, such as butylated-hydroxytoluene (BHT) or butylated hydroxyanisol (BHA).

An object of the present invention is to provide compositions comprising colorant-containing particles with improved light stability properties so that these compositions as well as cosmetic products which include them are less susceptible to fading or discoloration.

Another object of the present invention is to provide color compositions having an improved sunburn protection factor (SPF).

Yet a further object of the invention is to provide a process for making color compositions which have improved light stability and SPF properties.

These and further objects and advantages of the present invention will, upon reading the following specification, become apparent to those skilled in the field of color compositions.

SUMMARY OF THE INVENTION

It has been found that the objects and advantages described above are realized by compositions comprising colorant-containing particles which are coated with a composition comprising a suitable carrier component, such as titanium dioxide ($TiO_2$), and a propylene glycol component. This coating renders the colorant-containing particles resistant to degradation by ultra violet light and is therefore particularly useful for light sensitive colorants. Although carriers other than $TiO_2$ may be used as a coating component, the invention will be primarily described with reference to $TiO_2$. Accordingly, one aspect of the present invention is the novel color compositions comprising colorant-containing particles coated with titanium dioxide and propylene glycol. Another aspect of the invention is the novel process for preparing the coated color containing particles. A further aspect of the invention is the novel use of carriers such as titanium dioxide, in combination with propylene glycol to impart the property of improved light stability to the colorant-containing particles. And yet a further aspect of the invention is the novel use of titanium dioxide and propylene glycol to impart an improved SPF property to composition comprising colorant-containing particles.

DETAILED DESCRIPTION OF THE INVENTION

Figure 1:
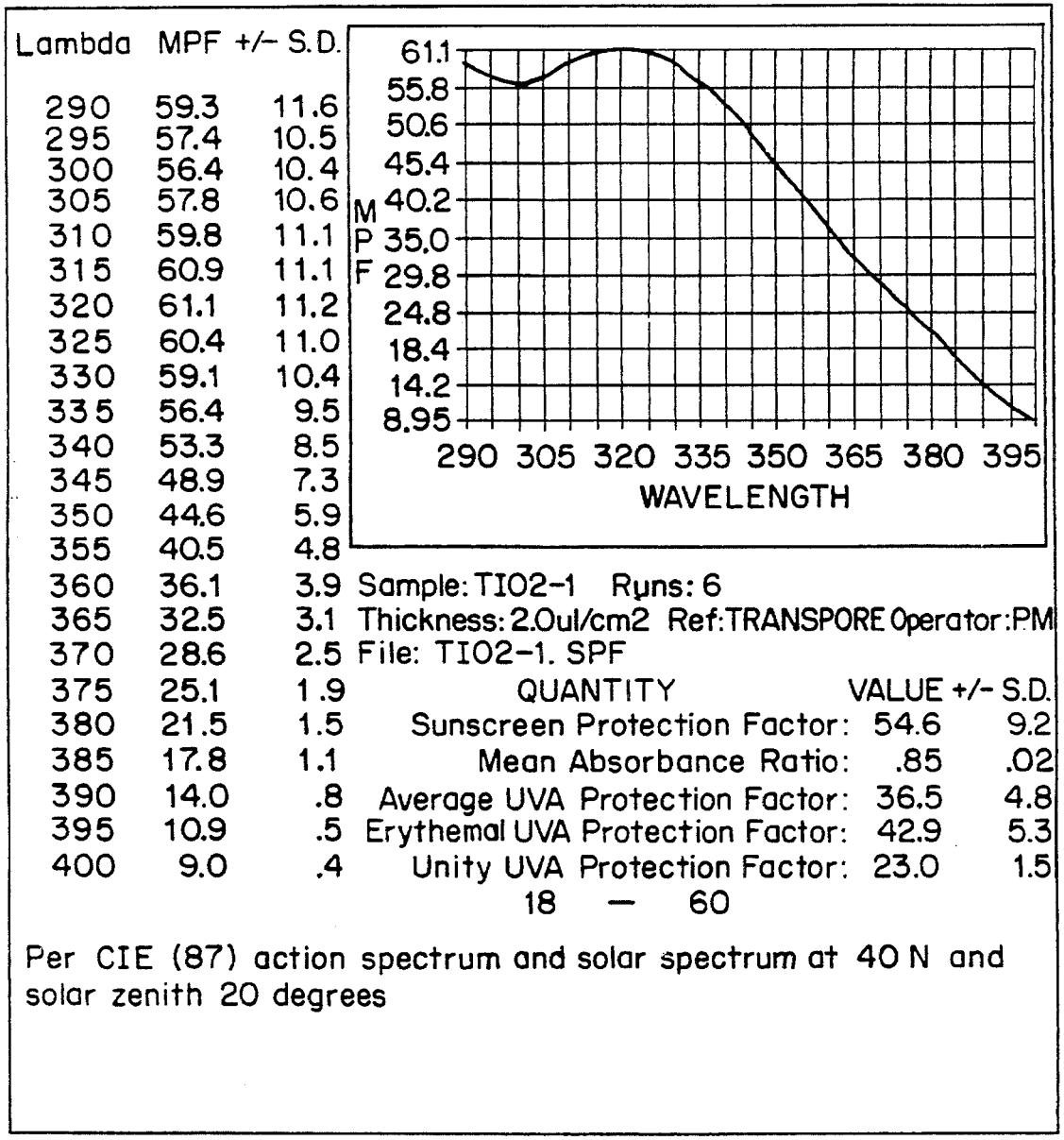
FIG. 1 shows SPF results for micronized $TiO_2$.

The present invention has been found to significantly improve both light stability and SPF properties of compositions comprising colorant-containing particles which are unstable in ultraviolet light. While such color compositions are used in a wide number of fields, e.g., paints and cosmetics, the following discussion will primarily be addressed to compositions for use in the cosmetic field; notwithstanding the fact that application of this invention embraces any and all fields where the stability of color compositions is desirable.

In accordance with the present invention, colored compositions are prepared by coating colorant-containing particles with a composition comprising propylene glycol and carrier particles.

As used herein, the term colorant-containing particles refers to any particle which imparts color useful in cosmetic, paint or similar compositions and particularly those which are light sensitive, i.e., susceptible to fading or discoloration. While colorant-containing particles include particles of inorganic pigments, e.g., iron oxides, the preferred colorant-containing particles comprise organic dyes laked onto a suitable carrier (substratum) such as $TiO_2$, and other such FD&C and D&C approved carriers. Specifically the dyes include, but are not limited to, the well-known FD&C and D&C dyes, for example, FD&C Blue No. 1, FD&C Yellow No. 5, Brown 13693, carmoisine edicol, FD&C No. 40, D&C Red 21 and D&C Red 27.

The colorant, which hereinafter unless indicated otherwise, will refer to FD&C and D&C dyes laked on to a suitable carrier in accordance with conventional dilution or slurry methods. While $TiO_2$ is a preferred carrier onto which the dye or suitable mixtures thereof is absorbed, other substrates include all FD&C and D&C approved substrates e.g., alumina, and zinc oxide, aluminum benzoate, calcium carbonate, etc. or combinations of such substrates.

Colorant-containing particles can be formed by absorbing an organic dye into substrate particles which are preferably in the form of micronized particles (average particle size of 0.05 to 0.4 microns). The resulting particles are then advantageously precipitated, dried and crushed to form a fine powder. The particle size depends on the type of pulverizing equipment used; however a particle size of about 0.2 to 0.3 microns is preferred and is obtained by using a Model No. 2D4 Pulverizer. Titanium dioxide is a preferred carrier for the colorant because of its superior sunscreen properties. However, since $TiO_2$ absorbs ultraviolet radiation, its use contributes to the degradation of the absorbed colorant (dye) which results in its fading and or discoloration.

The light stability of colorants, particularly those absorbed on a $TiO_2$ substrate is remarkably improved by coating the colorant particle with a coat comprising a carrier such as $TiO_2$, and propylene glycol. While the carrier $TiO_2$ is a preferred component of the coating composition, other suitable coating components include carriers such as zinc oxide and aluminum hydroxide. The carrier component is preferably micronized, i.e., having a particle size in the range of about 0.1 to about 0.3 microns. While these are the generally preferred parameters for the particle size of the carrier component, non-micronized particles may be used, however, the size of particles in the coating must of course be substantially smaller than the size of the colorant-containing particle onto which it is to be coated.

In addition to the carrier component, the coating composition further comprises propylene glycol. As will be apparent from the examples set forth below, the propylene glycol is preferably sprayed onto a homogeneous mixture of the colorant-containing particles and the micronized carrier. Nevertheless, however the propylene glycol is added to the mixture, it is desirable that the homogeneous mixture is uniformly contacted with propylene glycol and that the particles do not agglomerate when contacted with the propylene glycol. By adding to the colorant-containing particles a coating comprising a micronized carrier or mixtures thereof and the propylene glycol component, the coating acts as a protective barrier against radiation which causes fading and discoloration from reaching the colorant-containing particles.

The coating composition used in the present invention preferably contains the propylene glycol and the carrier component in a ratio of from about 1:4 to about 1:5 by weight. However, other suitable ratios of propylene glycol and carrier may be used. The ratio of coating composition to colorant-containing particle used to coat colorant-containing particles depends on the shade of the colorant which is desired, i.e., the more coating that is used the paler the shade of the colorant. The size of the resulting coated colorant-containing particles depends on both the initial particle size and the coating thickness. Nevertheless, generally final particle sizes of about 1 micron or less are suitable and micronized particle sizes are preferred especially for cosmetic uses, i.e., particularly for use as a sunscreen factor.

The following examples are provided in order to disclose the invention in the fullest possible extent and in the best mode known. Nevertheless they are to be construed as purely illustrative and not limiting of the present invention.

EXAMPLE 1

Procedure

In order to make 908 gms. of uncoated light stable micronized $TiO_2$ colored with FD&C Blue No. 1, the following procedure was followed:

The color load chosen was 1% by weight.

The 9.08 gms. of FD&C Blue No. 1 were dissolved in 3,500 ml of water. The solution was mixed well, until all the dye was completely dissolved. In a separate container, 10,000 ml of water was added and vigorously mixed, so as to slowly disperse 726 gms. of micronized $TiO_2$ having an average particle size of 0.1 microns. The dispersion was mixed for 15 minutes until dispersed completely using Yamato LR-41A Labo-Stirrer. Thereafter the dye solution (FD&C Blue No. 1) was added to the $TiO_2$ dispersion while mixing, and then continued to be mixed for 30 minutes to allow all the color to be absorbed by the $TiO_2$ particles. The volume was thereafter increased to 16,000 mls by the addition of tap water. The colorant-particle solution was then precipitated out by using an $AlCl_3$ solution, 32° Bé, diluted 1:1 with water.

After adding the $AlCl_3$ solution, the pH was checked and if necessary adjusted to be 3.0±0.3 with $AlCl_3$. Also, the bleed was checked, i.e., to determine the absence of unprecipitated dye, and once it was determined to be negative, the precipitant was filtered using a Buchner filtration apparatus with a Whatman qualitative #5 filter. The filtered product was dried in a Lindberg/Bleum laboratory oven Model No. SW-17TA-1 at a temperature between 70°–80° C. When fully dried, i.e., all moisture absent, the product was crushed and pulverized in a pulverizer Model No. 204 to a fine particle size having an average of about 0.2 to 0.3 microns.

The uncoated color particles were then placed in a Waring CB6 blender (Model No. 34 BL 22) and 182 gms. of micronized $TiO_2$ were added. The mixture was blended well until homogeneous and uniform. While blending, 136.2 gms of propylene glycol were uniformly sprayed (using a True-Temper pressure sprayer Model No. HS-200) onto the batch carefully so as to avoid any agglomeration of the particles and the batch was well blended until homogenous and uniform.

EXAMPLE 2

An alternative method of preparing uncoated particles of the colored $TiO_2$ lake is the slurry method. According to this method, 310 gms. of micronized $TiO_2$ (having an average particle size of about 0.1 microns) are dispersed in 500 gms. of water using a homogenizer. This mixture is homogenized until a low to medium viscosity suspension is obtained.

2.5 g. of a suitable FD&C (or D&C) dye is dissolved in 50 gms. of water, added to the blend, and mixed using a paddle mixer for 30 minutes until all the dye is absorbed by the $TiO_2$.

The dye is then precipitated with a $AlCl_3$ solution. Once the bleed is determined to be negative, the slurry is transferred and dried at 70°–80° C. When all the water has evaporated, the product is crushed and pulverized to a small particle size (having an average of about 0.2 to 0.3 microns. Thereafter a micronized $TiO_2$/propylene glycol coat is added, first by adding 55.14 g. micronized $TiO_2$ (average particle size 0.1 microns) and once homogeneous and uniform, 18.38 g. propylene glycol is uniformly sprayed onto the batch and the batch is mixed well until uniform. The light stability of the product made with the slurry method is similar to that obtained in Example 1.

EXAMPLE 3

Samples of both the uncoated colorant particles and coated colorant particles prepared in accordance with Example 1 were placed in 1 oz. clear plastic vials and exposed for 24 hours to the following sources of radiation:

—shortwave ultraviolet

—longwave ultraviolet

—white light 3600° Kelvin (approximate)

—north sky light 7000° K. (approximate)

After the 24 hour exposure, samples of the uncoated colorant particles showed, in all cases, complete fading and developed an off-white to gray-white color. The samples of the coated colorant particles, i.e., those which were coated with the micronized $TiO_2$ and propylene glycol showed none to slight color loss, maintaining the characteristics of their original color.

Additional tests were performed using other dyes such as FD&C Yellow No. 5, Brown 13693, and carmoisine edicol, and all showed the same results as the FD&C Blue No. 1.

EXAMPLE 4

The SPF effectiveness of the micronized $TiO_2$/propylene glycol coated titanium dioxide particles was established by comparing the following two samples:

—micronized $TiO_2$ (Sample 1)

—micronized $TiO_2$ and 5% by weight of propylene glycol (Sample 2)

The latter sample was prepared by spraying 95 g. of micronized $TiO_2$ (average particle size of 0.1 micron) with 5 g. of propylene glycol and mixing the sprayed $TiO_2$ particles well to insure a homogeneous mixture.

Figure 2:
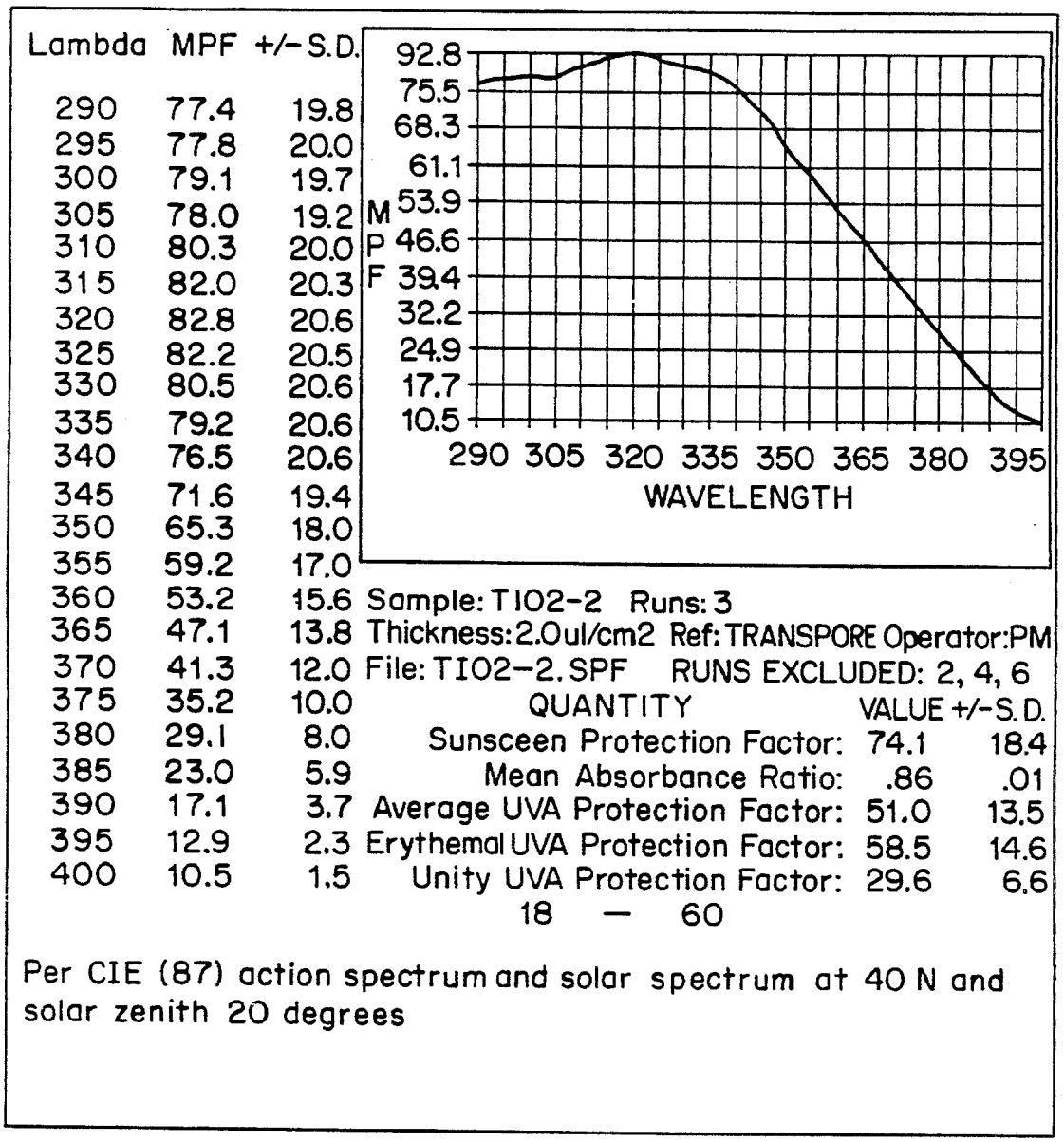
FIG. 2 shows SPF results for micronized $TiO_2$ and 5% by weight of propylene glycol.

A 20% dispersion of each of the above samples in isopropyl myristate was prepared. Each sample was thereafter measured to determine its SPF (sun protection factor) using a SPF-290 spectrophotometer (Optometrics USA). The results are shown in FIGS. 1 and 2. FIG. 1 shows SPF results for sample 1. FIG. 2 shows SPF results for sample 2.

By comparing the two graphs, it was concluded that the addition of 5% propylene glycol to the $TiO_2$ particles significantly increased the SPF value of the $TiO_2$ when used as a Sunscreen agent. It should be noted that during the measurement, six runs were taken on each sample. Because of the fact that for the $TiO_2$/propylene glycol (Sample 2) the average was off the instrument's scale, runs 2, 4, and 6 were excluded in order to plot a curve within the instrument's capability (maximum 99.99).

We claim:

1. A method of improving the stability of colorant-containing particles which are degraded by ultraviolet light, comprising contacting said particles with a coating comprising propylene glycol and a carrier component selected from the group consisting of titanium dioxide, zinc oxide, aluminum hydroxide and mixtures thereof wherein the coating is present in an amount sufficient to form a protective barrier against light which causes fading and discoloration of the colorant-containing particles.

2. A method of improving the sunburn protection factor (SPF) of a cosmetic composition comprising a colorant-containing particle, comprising coating said colorant-containing particle with propylene glycol and a carrier selected from the group consisting of titanium dioxide, zinc oxide, aluminum hydroxide and mixtures thereof wherein the coating is present in an amount effective to impart improved SPF properties to the cosmetic composition.

3. A method according to claim 2, wherein the carrier is titanium dioxide.

4. A method according to claim 1 wherein the ratio of propylene glycol to carrier component is from about 1:4 to 1:5 by weight.

5. A method according to claim 2 wherein the ratio of propylene glycol to carrier component is from about 1:4 to 1:5 by weight.

* * * * *